United States Patent [19]

Bazin et al.

[11] Patent Number: 5,198,875
[45] Date of Patent: Mar. 30, 1993

[54] DEVICE DESIGNED TO ASSESS THE BRIGHTNESS OF A SURFACE MORE PARTICULARLY OF THE SKIN

[75] Inventors: Roland Bazin, Vitry-sur-Seine; Luc Chommeloux, Antibes; Gérard Obadia, Nice; Hervé Chardron, Longjumeau, all of France

[73] Assignee: L'Oreal, Paris, France

[21] Appl. No.: 742,754

[22] Filed: Aug. 9, 1991

[30] Foreign Application Priority Data

Aug. 16, 1990 [FR] France ................... 90 10379

[51] Int. Cl.⁵ ............... G01N 21/57; G01N 33/483
[52] U.S. Cl. .................................................. 356/369
[58] Field of Search ............ 356/364, 369, 237; 250/225

[56] References Cited

U.S. PATENT DOCUMENTS

| | | | |
|---|---|---|---|
| 2,866,375 | 12/1958 | Wells. | |
| 2,947,212 | 8/1960 | Woods | 356/369 |
| 3,060,793 | 10/1962 | Wells | 356/369 |
| 3,904,293 | 9/1975 | Gee | 356/369 |
| 4,398,541 | 8/1983 | Pugliese | 128/665 |
| 4,482,250 | 11/1984 | Hirvonen et al. | 356/369 |
| 4,846,184 | 7/1989 | Comment et al. | 356/445 |

FOREIGN PATENT DOCUMENTS

| | | |
|---|---|---|
| 0198759 | 10/1986 | European Pat. Off.. |
| 0335163 | 10/1989 | European Pat. Off.. |
| 2175259 | 10/1973 | France. |
| 2499717 | 8/1982 | France. |
| 2650890 | 2/1991 | France.. |

OTHER PUBLICATIONS

Patent Abstracts of Japan vol. 13 No. 475 (P-950) [3823] Oct. 27, 1989.
Vol. 5 No. 32 (P. 50) (704) Feb. 27, 1991.
IBM Technical Disclosure Bulletin vol. 27 No. 9 Feb. 1985.

*Primary Examiner*—Richard A. Rosenberger
*Attorney, Agent, or Firm*—Cushman, Darby & Cushman

[57] ABSTRACT

A device for measuring the brightness of a surface includes a light source to send an incident beam onto the surface and a polarizer and two analyzers one for analyzing the reflected light and the other for analyzing the diffuse reflection from the surface at a selected point of incidence; light-sensitive photodetector means are provided to receive light from the analyzers; the incident light impinges on the surface under examination at an angle of between 0° and 90° with the incident beam polarization being perpendicular to the plane of incidence; the analyzers are located to differentiate between parallel and perpendicular polarization to provide differences in the assessment of specular and diffuse brightness.

9 Claims, 2 Drawing Sheets

DEVICE DESIGNED TO ASSESS THE BRIGHTNESS OF A SURFACE MORE PARTICULARLY OF THE SKIN

FIELD OF THE INVENTION

The invention concerns a device for assessing the brightness of a surface and comprising a light source to emit an incident beam on the surface under examination, means comprising a polariser and at least an analyser for analysis of the reflection either with a parallel orientation of the polariser and analyser directions, or with a right angle orientation of the said directions, the polariser being located between the light source and the surface, whereas the analyser is located along the path of the reflected beam, photodetector means sensitive to the light returned by the surface also being provided.

The invention concerns more particularly though not exclusively, a device for assessing skin brightness.

DESCRIPTION OF THE PRIOR ART

The applicant has already submitted a prior patent application FR 89-10 709, filed on Aug. 7, 1989, for a device of this type. Tests carried out have shown that such a device, while giving satisfactory results was of relatively reduced sensitivity and discriminatory power.

The purpose of the invention is mostly to provide a device for assessing surface brightness, particularly of the skin, which is more sensitive and more discriminating and allows differentiation of certain types of brightness by its directivity properties. It is also desirable that the device allow measurement over a reduced almost pinpoint area, regardless of the colour.

SUMMARY OF THE INVENTION

According to the invention, a device designed to assess the brightness of a surface, particularly of the skin, as previously defined, is characterised by the fact that the light source is directional and that the polarised beam impinges on the surface for examination with an angle of incidence between 0° and 90°, limits being excluded; that the incident beam polarisation direction is perpendicular to the plane of incidence; that it is arranged to measure the reflection in at least two different reflection directions, one reflection direction being mainly symmetrical with the incident direction as related to the perpendicular to the surface; and that for each reflection direction, means are also provided to define the difference between reflection with parallel polarisation and analysis directions, and reflection with perpendicular polarisation and analysis directions, such determined differences constituting an assessment of the so-called specular brightness and the so-called diffuse brightness.

The polarised beam angle of incidence on the surface is advantageously approximately 45° to the perpendicular.

The second direction of reflection under consideration is advantageously located within a range of more or less 10° on either side of the perpendicular to the examined surface. This second direction is preferably effectively perpendicular to the said surface; it is generally located in the plane of incidence.

The analyser means comprise for each reflection direction under examination, a system allowing angular separation of the polarised luminous signals parallel and perpendicular to the plane of incidence; two photodetectors are advantageously associated with each separator system to allow simultaneous measurement of these luminous signals.

Each separator system advantageously consists of a polarisation separator cube.

Such a device may be used to study biological phenomena influencing skin brightness, for instance sebaceous secretion kinetics, or to study the consequences on brightness of the skin of the application of cosmetic products, particularly the aptitude of a mat base product to reduce cutaneous brightness caused by the sebum.

Apart from the items outlined above, the invention consists of a given number of other provisions which will be referred to more explicitly hereinafter with regard to a non restrictive example of implementation described in detail with reference to the appended drawings.

DETAILED DESCRIPTION OF THE INVENTION

Figure 1:
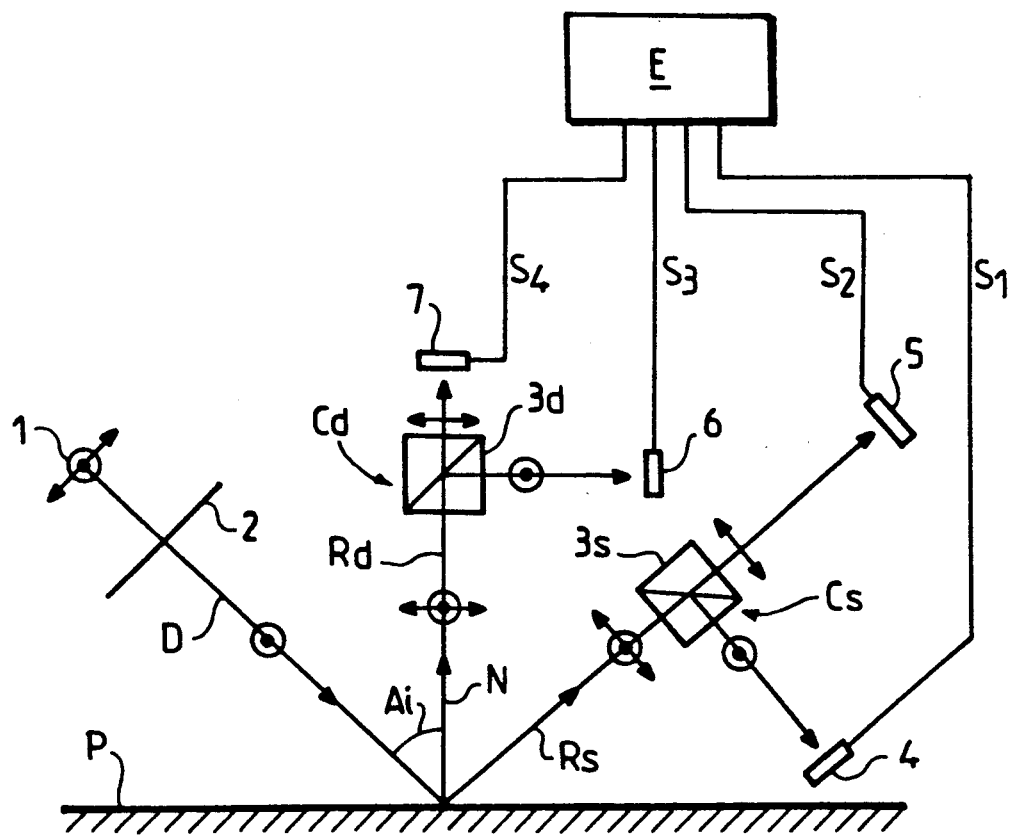
FIG. 1 of the drawings is a sketch of the device according to the invention.

Referring to FIG. 1, this shows the sketch of a device for assessing the brightness of a surface P, and more particularly the skin.

The device comprises a non-polarised light source 1. In the sketch the non-polarised light is symbolically represented by a circle with a point at the centre, bisected by a double arrow along the diameter; a light polarised perpendicularly to the plane of incidence is represented by a circle with a point at the centre, whereas a light polarised parallel with the plane of incidence is simply represented by a double arrow.

The light source 1 is a directive white light source, complete for instance with an optical system (not shown here) producing a parallel beam along direction D. A rectilinear polariser 2 is located with its mean plane orthogonal with direction D, between source 1 and surface P so that the light falling on the skin along direction D is polarised.

The angle of incidence A1 formed between direction D of the incident beam and direction N perpendicular to surface P is included between 0° (perpendicular incidence) and 90° (sweeping incidence) exclusive. Angle A1 is preferably equal to 45°, as shown in FIG. 1 or close to that value.

The incident beam polarisation direction after passing through polariser 2 is perpendicular to the plane of incidence. The device is arranged to measure the reflection along two different reflection directions Rs, Rd. Direction Rs corresponding with the specular reflection is symmetrical with direction D as related to the perpendicular N. The light reflected along direction Rd is obtained by diffuse reflection of the light which has penetrated inside the skin P, or by a surface reflection, it shows a certain irregularity.

The second reflection direction Rd selected for measurements is preferably integrated with direction N, or close to that direction, within more or less 10°. This direction Rd is preferably located in the plane of incidence.

The light reflected along the two directions Rs and Rd is no longer polarised in linear manner, contrary to the incident light.

Analyser means Cs, Cd are provided for each examined direction and comprise a separator system, advantageously consisting of a polarisation separator cube $3s$, $3d$, of the Wollaston prism type, allowing in the example considered here a right angled angular separation of luminous signals polarised parallel and perpendicular to the plane of incidence, for each reflected beam Rs, Rd.

Two photodetectors 4, 5 and 6, 7 respectively, are associated with each separator system to allow simultaneous measurement of luminous signals. The photodetectors are linked with electronic means E allowing processing of signals to provide the required results.

Photodetector 4 receives the Rs reflected beam fraction polarised perpendicularly to the plane of incidence and provides a signal S1.

Photodetector 5 receives the Rs reflected beam fraction polarised parallel with the plane of incidence and provides a signal S2.

Photodetector 6 receives the Rd reflected beam fraction polarised perpendicularly to the plane of incidence and provides a signal S3.

Finally, photodetector 7 receives the Rd reflected beam fraction polarised parallel with the plane of incidence and provides a signal S4.

For each reflection direction Rs, Rd, the beam has an intensity component Ib, due essentially to surface brightness, and an intensity component Ic originating the colour of the surface under consideration, coming from a part of the light which has penetrated the environment wherein it has undergone diffraction phenomena before return to the photodetectors. In practice this can be expressed as:

$$S1 = (Ib + \tfrac{1}{2}Ic)e,$$

$$S2 = (\tfrac{1}{2}Ic)s,$$

for beam Rs representing the specular reflection.

The following can be expressed for beam Rd representing diffuse reflection:

$$B3 = (Ib + \tfrac{1}{2}Ic)d,$$

$$S4 = (\tfrac{1}{2}Ic)d,$$

The difference between the two results S1 and S2 gives value $S1 - S2 = (Ib)s$ which is a measure of the brightness in direction Rs, a brightness which may be deemed specular brightness Bs.

The difference between results S3 and S4 gives the expression $S3 - S4 = (IB)d$ being the brightness in Rd direction, and which may be deemed diffuse brightness Bd.

Results S1, S2, S3 and S4 can be displayed on a screen by electronic means E and the differences can be obtained manually.

According to another possibility, electronic means E are arranged to ensure direct differentiation between signals S1 and S2 on the one hand, and signals S3 and S4 on the other hand, and to display these differences, i.e. to display the specular brightness Bs and the diffuse brightness Bd.

The device according to the invention has a remarkable capacity to differentiate between the two types of brightness Bs and Bd. In case of marked relief signs of the skin, brightness directivity will be low and the specular brightness value Bs will only be somewhat greater than diffuse brightness Bd.

On the other hand if the skin surface is very smooth, for example after cosmetic product treatment, the brightness will be much more directional and specular brightness value Bs will be distinctly greater than diffuse brightness Bd.

Figure 2:
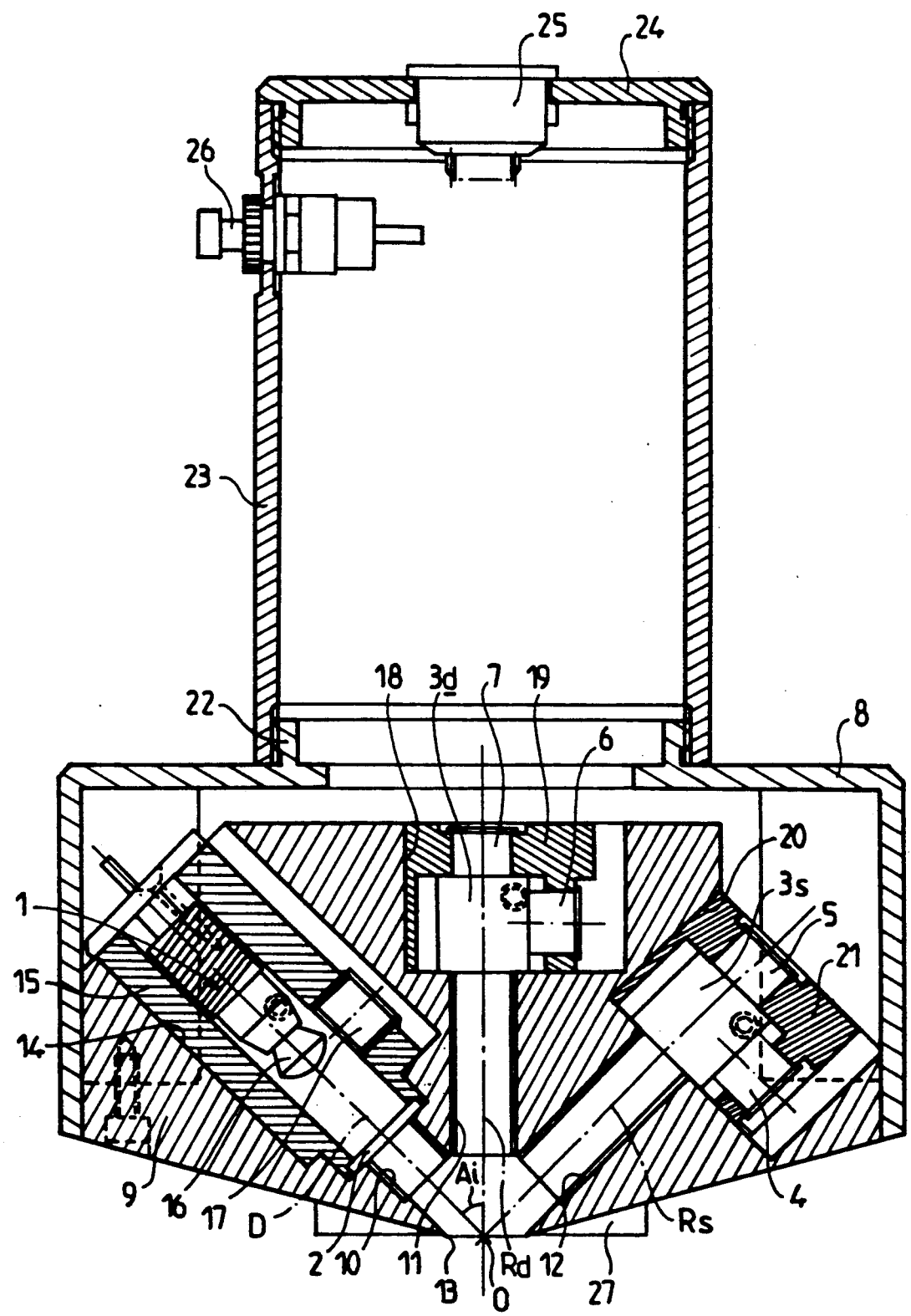
FIG. 2 is a vertical section through the device according to the sketch in FIG. 1.

Referring to FIG. 2 this shows the design for a device according to the sketch in FIG. 1.

The device has a base 8 removably retaining a core 9 with three recesses 10, 11, 12 in the axes of directions D, Rd and Rs respectively. These recess axes come together at point O forming the centre of an elliptical opening 13 in the lower part of the core and applied to the surface P under examination.

On the opposing side of point O, the recess 10 extends into a larger diameter chamber 14 wherein a sleeve 15 is located coaxially with direction D. Inside the sleeve is the light source 1 with light bulb 16, fitted for example with a lens providing a directive beam. A photodetector element 17 is mounted in the wall of the sleeve 15, at the level of the light output from bulb 16 to measure the average light intensity of the source. This element 17 is connected to electronic means not shown here, designed to modulate the measurement results from photodetector 4-7 in accordance with the light source intensity.

Recess 11 extends on the opposing side of point O, into a chamber 18 wherein is located a unit 19 comprising the polarisation separator cube $3d$ and associated photodetectors 6, 7.

On the side opposing point O, recess 12 extends likewise into a cylindrical chamber 20 wherein a unit 21 is located respectively comprising the separator cube $3s$ and photodetectors 4, 5.

It should be noted that using 45° as A1 angle value; the symmetrical direction to the perpendicular for Rs; and the perpendicular for Rd, it is possible to house the whole of the light source, the separator cubes and photodetectors within a minimal volume.

The base 8 has in its central upper part, an aperture surrounded by a collar 22 on which is retained by screwing, a tubular component closed at the top by a flat cover 24. The centre of the cover has an electrical connector 25, for external electrical connections, more particularly to transmit results from photodetector components 4,5,6,7 and 17 linked to the connector. A push-button 26 is mounted in the wall of the element 23; this push-button 26 controls the light source 16 for a given period during which the measurement is recorded. The light is switched OFF manually with the push-button 26, or automatically. The various electrical connections are not illustrated within the base 8 and the tubular component 23 which also form means for manual holding and application of the assembly forming the measuring head.

It should be noted that the lower end of the core 9 forms a truncated cone, the smaller base consisting of the aperture 13. To ensure satisfactory bearing of the measuring head on surface P, a crown 27 can be provided, with its lower edge effectively located in the plane of the aperture 13.

The device shown in FIG. 2 is used in accordance with the following procedure.

The operator holds the device by the cylindrical part of the tubular component 23 and applies point O to the centre of the area to be measured. Then depressing the push-button 26, the operator triggers the measurement at that point.

The device according to the invention, allowing the quantification in space of the brightness phenomena in two different directions is particularly interesting for brightness measurements of the skin, subject to surface irregularities. The light reflected by the surface of the skin may be diffused in various directions and not exclusively in the specular direction, where it remains at its maximum. The device according to the invention takes this phenomenon into account.

It can be said that the skin brightness results from the intrinsic brightness of the skin and its surface condition.

It will be noted that as a result of the polarisation separator cubes 3s, 3d, no mechanical movement is required between the polariser and analyser, thus improving the accuracy of the device and allowing simultaneous measurement of signals polarised in parallel and perpendicular to the plane of incidence.

We claim:

1. Apparatus, for assessing the brightness of a surface such as skin, comprising
    a light source for projecting an incident beam of light on the surface to be examined, means comprising a polarizer and analyzer means for assessing the light reflected from the surface with one of a parallel and a right angle orientation of polarization relative to said polarizer and analyzer means, said polarizer being disposed between said light source and the surface, said incident beam producing reflected beams, said apparatus including a photodetector means sensitive to the light reflected from the surface, said light source being capable of producing a directed beam positioned to impinge on the surface at a selected angle of incidence between 0° and 90°; said incident beam being polarized by said polarizer and being reflected from the surface in at least two directions with one of said directions being symmetrical with the incident beam's direction of propagation relative to a normal axis to the surface; said analyzer means being positioned to intercept beams reflected from the surface in each of said two directions and to provide a differentiation between the reflection with parallel polarization and the reflection with perpendicular polarization with the differences obtained representing an assessment of specular brightness and diffuse brightness.

2. Device according to claim 1, characterised in that the angle of incidence of the incident beam is approximately 45° to the perpendicular, the angle of the one of said reflection direction also being close to 45°.

3. Device according to claims 1 or 2, characterised in that the other reflection direction is located in a range of approximately 10° on either side of direction (N) perpendicular to the surface under examination.

4. Device according to claim 3, characterised in that the second reflection direction is effectively perpendicular to the said surface.

5. Device according to claim 1, characterised in that, for each reflection direction under consideration, the analyser means comprise a system allowing the angular separation of luminous signals polarised in parallel and perpendicular to the plane of incidence.

6. Device according to claim 5, characterised in that the two photodetectors are associated with a separator system to allow simultaneous measurement of the luminous signals.

7. Device according to claims 5 or 6, characterised in that each separator system (Cs, Cd) consists of a polarisation separator cube (3s, 3d).

8. A process for studying the sebaceous secretion kinetics of skin using an apparatus for assessing the brightness of skin surface comprising
    a light source for projecting an incident beam of light on the surface to be examined, means comprising a polarizer and analyzer means for assessing the light reflected from the surface with one of a parallel and a right angle orientation of polarization relative to said polarizer and analyzer means, said polarizer being disposed between said light source and the surface, said incident beam producing reflected beams, said apparatus including a photodetector means sensitive to the light reflected from the surface, said light source being capable of producing a directed beam positioned to impinge on the surface at a selected angle of incidence between 0° and 90°; said incident beam being polarized by said polarizer and being reflected from the surface in at least two directions with one of said directions being symmetrical with the incident beam's direction of propagation relative to a normal axis to the surface; said analyzer means being positioned to intercept beams reflected from the surface in each of said two directions and to provide a differentiation between the reflection with parallel polarization and the reflection with perpendicular polarization with the differences obtained representing an assessment of specular brightness and diffuse brightness.

9. The method of achieving a mat appearance to reduce the brightness of skin due to the sebum comprising the step of using an apparatus for assessing the brightness of skin comprising
    a light source for projecting an incident beam of light on the surface to be examined, means comprising a polarizer and analyzer means for assessing the light reflected from the surface with one of a parallel and a right angle orientation of polarization relative to said polarizer and analyzer means, said polarizer being disposed between said light source and the surface, said incident beam producing reflected beams, said apparatus including a photodetector means sensitive to the light reflected from the surface, said light source being capable of producing a directed beam positioned to impinge on the surface at a selected angle of incidence between 0° and 90°; said incident beam being polarized by said polarizer and being reflected from the surface in at least two directions with one of said directions being symmetrical with the incident beam's direction of propagation relative to a normal axis to the surface; said analyzer means being positioned to intercept beams reflected from the surface in each of said two directions and to provide a differentiation between the reflection with parallel polarization and the reflection with perpendicular polarization with the differences obtained representing an assessment of specular brightness and diffuse brightness.

* * * * *